United States Patent [19]
Fischell et al.

[11] Patent Number: 5,639,274
[45] Date of Patent: Jun. 17, 1997

[54] INTEGRATED CATHETER SYSTEM FOR BALLOON ANGIOPLASTY AND STENT DELIVERY

[76] Inventors: Robert E. Fischell, 14600 Viburnum Dr., Dayton, Md. 21036; Tim A. Fischell, 1018 Chancery La., Nashville, Tenn. 37215; David R. Fischell, 71 Riverlawn Dr., Fair Haven, N.J. 07704

[21] Appl. No.: 458,471

[22] Filed: Jun. 2, 1995

[51] Int. Cl.$^6$ ................................. A61M 29/00
[52] U.S. Cl. .................. 604/96; 604/104; 606/108; 606/194
[58] Field of Search .................. 604/96, 102, 104, 604/160, 161, 171, 264, 280; 606/195, 191, 198, 200, 108, 194; 623/1, 12, 11

[56] References Cited

U.S. PATENT DOCUMENTS

| | | | |
|---|---|---|---|
| 4,955,895 | 9/1990 | Sugiyama | 606/194 |
| 4,969,890 | 11/1990 | Sugita et al. | 606/192 |
| 5,019,090 | 5/1991 | Pinchuk | 606/194 |
| 5,092,877 | 3/1992 | Pinchuk | 623/1 |
| 5,192,297 | 3/1993 | Hull | 606/195 |
| 5,266,073 | 11/1993 | Hall | 623/1 |
| 5,344,426 | 9/1994 | Lau et al. | 606/198 |
| 5,456,694 | 10/1995 | Marin et al. | 606/198 |
| 5,484,444 | 1/1996 | Braunschweiler et al. | 606/108 |
| 5,507,768 | 4/1996 | Lau et al. | 606/198 |

*Primary Examiner*—Robert A. Hafer
*Assistant Examiner*—Chalin Smith
*Attorney, Agent, or Firm*—Morton J. Rosenberg; David I. Klein

[57] ABSTRACT

This invention is directed to an integrated catheter system (60) including a stent catheter (65) and a balloon angioplasty catheter (20). The balloon angioplasty catheter (20) has an inflatable balloon (23) mounted near the catheter's distal end which is initially used for dilation of a vessel at a low balloon pressure to partially inflate the balloon (23). The stent catheter (65) contains a stent (15) within a stent containment cavity (69) and the stent (15) is displaced over the balloon (23). The stent (15) is held in place over the partially inflated balloon (23) and an outer tube (62) of the stent catheter (65) is pulled back. The stent (15) is deployed and the balloon (23) is reinflated to a higher pressure to embed the stent (15) into the wall of the vessel.

15 Claims, 9 Drawing Sheets

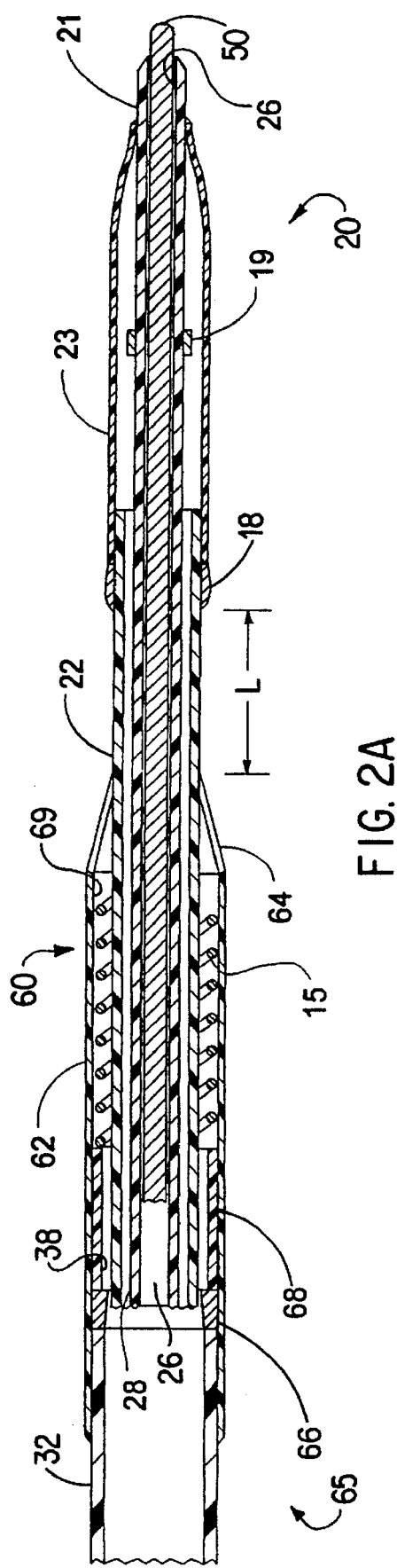
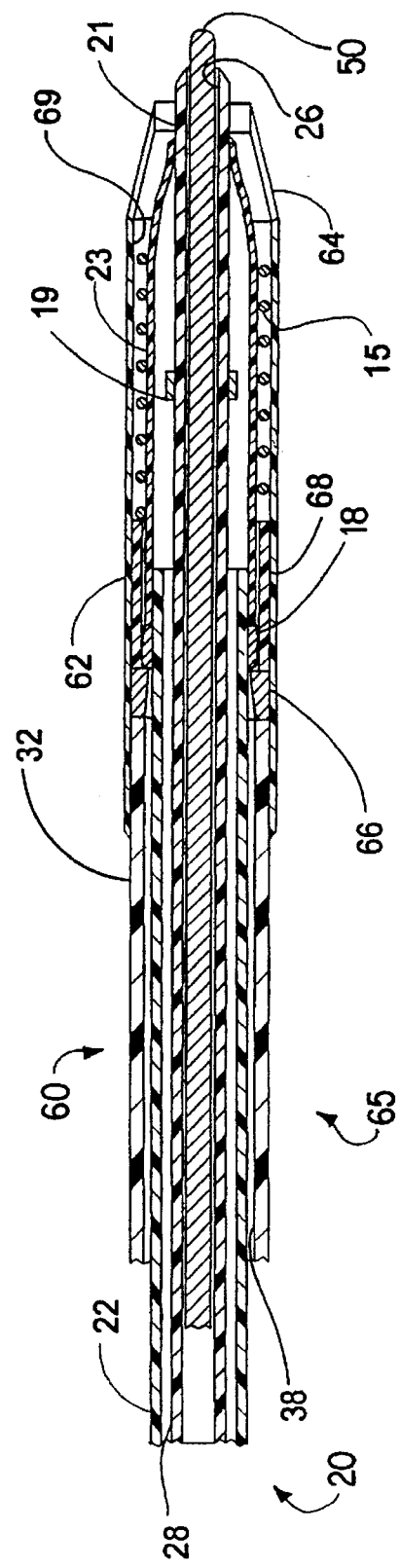
FIG. 2A
FIG. 2B

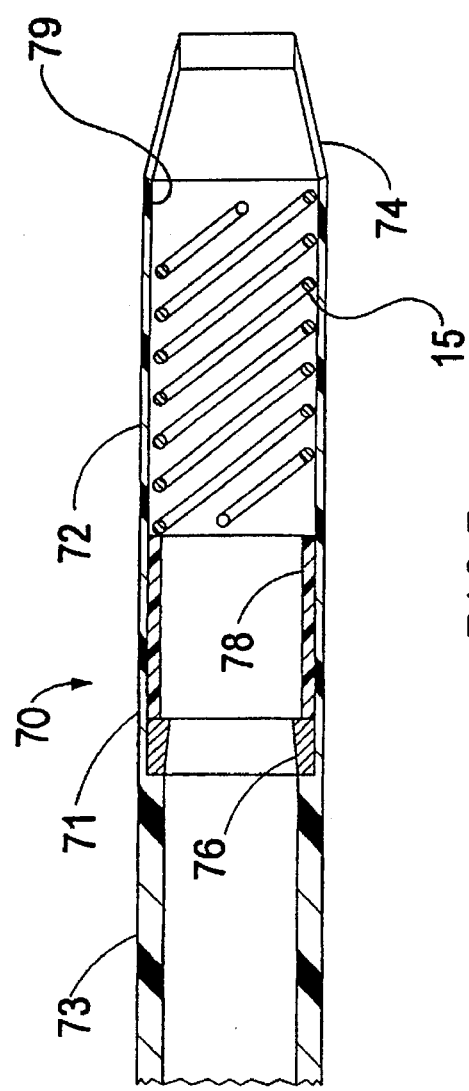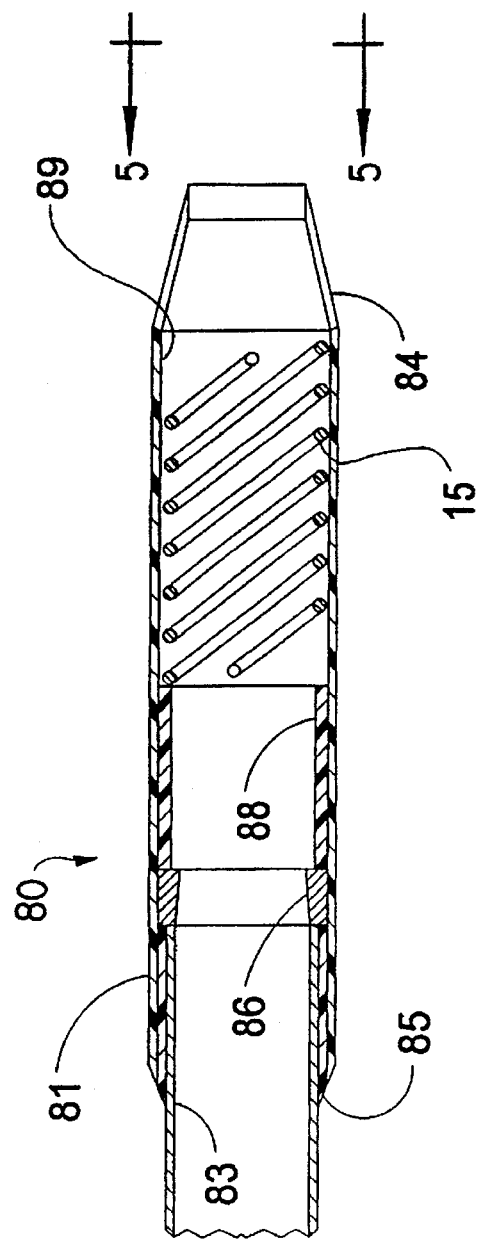

INTEGRATED CATHETER SYSTEM FOR BALLOON ANGIOPLASTY AND STENT DELIVERY

This invention is generally in the field of devices for opening and maintaining patency within vessels of the human body with specific application to percutaneous transluminal coronary angioplasty (PTCA) and stent delivery into a dilated arterial stenosis.

BACKGROUND OF THE INVENTION

It is well known to use balloon angioplasty catheters for the dilatation of various vessels of the human body and most particularly for opening stenotic arteries. It is also well known to place stents into vessels to maintain patency of that vessel. It is also well known to use a balloon catheter for imbedding a stent into the wall of the vessel to prevent stent migration.

It is typical to use separate catheters for vessel dilatation and for stent delivery. This requires one or more catheter exchanges which increases the time and cost for performing interventional procedures. Since the patient is typically in some discomfort during such procedures, it is also highly advantageous to the patient to make the interventional procedure as short as possible. Furthermore, removing a balloon angioplasty catheter after balloon dilatation can expose an intimal dissection that can make stent placement more difficult.

In U.S. Pat. No. 5,019,090, L. Pinchuk illustrates in FIGS. 13 to 18 a method for mounting a self-deploying stent on a balloon angioplasty catheter. However, Pinchuk's method functions only for self-deploying stents and not balloon expandable stents, and furthermore, his method requires the balloon to be advanced at least 3 cm beyond the distal end of the stenosis that is treated. That is not possible in many coronary arteries because of restrictions in the distal length of the coronary arteries. Furthermore, Pinchuk's method requires two additional steps, i.e. one is a further advancement of the balloon after balloon angioplasty is performed, and later pulling the balloon back within the deployed stent. Pulling back of the balloon catheter can cause the stent to be moved away from its optimal location. Additional steps in such a procedure require additional time which is generally undesirable. Furthermore, Pinchuk does not teach a means or method for the use of a guide wire through the center of the integrated catheter so as to guide it through the typically tortuous coronary vasculature. Still further, Pinchuk teaches an outer sheath with a blunt end whose operability can be defeated because of intimal dissection which often occurs as a result of balloon angioplasty or atherectomy. Still further, Pinchuk does not describe any structure at the catheter's proximal end for the introduction of fluids and a guide wire and for disallowing inadvertent release of the stent. Still Further Pinchuk requires two separate tubes for stent placement which is more complex than the use of a single tube for stent placement.

In U.S. Pat. No. 5,266,073 by W. H. Wall, there is described an "Angioplasty Stent" wherein a stent is mounted onto the exterior surface of a catheter, which catheter is placed coaxially over a conventional balloon angioplasty catheter. The Wall invention has several disadvantages and probably his design concept is not actually functional. By wrapping the stent around and onto the exterior surface at the distal end of the stent catheter, the stent can be easily dislodged as it is advanced through the tortuous coronary vasculature. Dislodgment would be less of a problem if close to 100% of the length of the stent is placed over the stent catheter; but in that case, the balloon at the distal end of the balloon angioplasty catheter could not be used to expand the stent. If, on the other hand, most of the length of the stent is placed beyond the distal end of the catheter onto which it is mounted so that the balloon could be used (though not efficiently) to expand the stent, then in that case the stent, as previously described, could easily become dislodged from the distal end of its catheter. Still further, having a stent mounted on the exterior surface of a catheter can cause a great deal of abrasion of the endothelial tissue on the inside surface of the arteries which is highly disadvantageous. Furthermore, the Wall invention could not be used with a self-expanding stent which stent has several functional advantages. Still further, Wall does not teach either a means to prevent distal embolization of the stent beyond the end of the balloon, nor does he teach a means for accurately positioning the stent onto the balloon.

SUMMARY OF THE INVENTION

The present invention overcomes the disadvantages of prior art devices by integrating a balloon catheter and a single tube stent delivery catheter into an integrated catheter system which can perform both balloon angioplasty and stent delivery. Although this invention could be used for any vessel of the human body including but not limited to arteries, veins, vascular grafts, billiary ducts, urethras, fallopian tubes, bronchial tubes, etc., the descriptions herein will highlight the use of this device for arterial balloon angioplasty (and specifically PTCA) followed by intraarterial stenting.

No prior art known to the applicants teaches means for:

(1) precisely positioning the stent located at the distal end of a stent delivery catheter onto the balloon prior to stent expansion, (2) disallowing the stent from being inadvertently released beyond the distal end of the balloon angioplasty catheter thus resulting in a distal embolilzation of the stent, (3) using a tapered nose cone at the distal end of the stent catheter into which the stent is placed to assist in placement of the stent onto the balloon angioplasty catheter, (4) being capable of using either a balloon expandable stent or a self-expanding stent whichever is better suited for a particular vascular application, and (5) obtaining all the above listed advantages with the use of single tube, stent delivery catheter.

Thus an object of this invention is to perform vessel dilatation, stent placement, and balloon enhanced embedding of the stent into the vessel wall all with a single integrated catheter.

Another object of this invention is to allow the balloon to remain in one place in the artery during (1) balloon angioplasty, (2) stent placement, and finally (3) the further imbedding of the stent into the arterial wall.

Still another object of this invention is to deploy a self-expanding stent by means of pulling back a slideable stent catheter while holding the stent onto the balloon which allows the stent to expand radially outward into a dilated stenosis.

Still another object of this invention is to provide an improved apparatus and method for deploying balloon expandable stents.

Still another object of this invention is to have the integrated catheter capable of being advanced over a flexible guide wire.

Still another object of this invention is to provide a conically shaped distal section of the stent catheter which can accomplish proper placement of the stent even in cases of severe intimal dissection which could cause an intimal flap that could block the passage of a stent delivery catheter having a blunt end.

Still another object of this invention is to initially position the non-deployed stent at least several centimeters proximal to the proximal end of the angioplasty balloon thus allowing better trackability of the catheter's distal end over a flexible guide wire and through tortuous coronary arteries and through a long tight stenosis.

Still another object of this invention is to have an optimum means to limit the forward displacement of the stent so as to prevent the stent from being inadvertently released beyond the distal end of the balloon angioplasty catheter.

Still another object of this invention is to provide a means to precisely position the stent onto the balloon after the integrated system has been placed in an artery.

These and other objects and advantages of this invention will become apparent to a person of ordinary skill in this art upon careful reading of the detailed description of this invention including the drawings and claims as presented herein.

BRIEF DESCRIPTION OF THE DRAWINGS

FIG. 2A is a longitudinal cross section of the distal section of a preferred embodiment of the integrated catheter system.

FIG. 2B is a longitudinal cross section of the same embodiment as FIG. 2A with the stent catheter advanced to its most forward position over the balloon angioplasty catheter.

FIG. 3 is longitudinal cross section of a distal section of an alternative embodiment of the stent delivery catheter.

FIG. 4 is longitudinal cross section of a distal section of another alternative embodiment of the stent delivery catheter.

FIG. 7E shows the stent catheter pulled back thus releasing a self-expanding stent so that it deploys radially outward against the vessel wall.

DETAILED DESCRIPTION OF THE INVENTION

Three prior U.S. patent applications (Ser. Nos. 08/273, 459, 08/298,214 and 08/351,498) by the same inventors (which are included herein by reference) describe various means for delivering self-expanding, shape memory metal stents or balloon expendable stents into a vessel of the human body. The invention described herein expands the concepts taught in those prior applications by teaching a simplified integrated catheter system that has an expandable balloon located near the catheter's distal end whose purposes are to initially dilate a vessel at a comparatively low balloon pressure, then hold the stent in place over a slightly inflated balloon while the stent delivery catheter is pulled back; then after the stent is deployed, reinflating the balloon to a higher pressure to imbed the stent into the wall of the vessel. The balloon can also be used to deploy a stent if the stent is not self-expandable. The present design is capable of performing these functions while retaining the balloon at one single longitudinal position within the artery, i.e., at no time is there a need to advance the balloon beyond the dilated stenosis.

Figure 1:
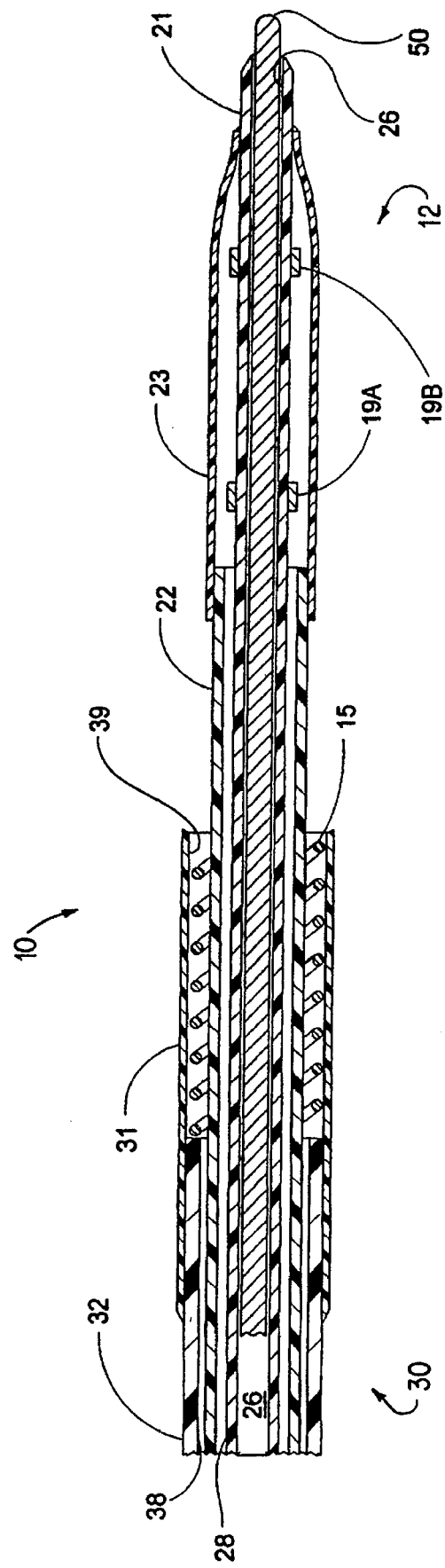
FIG. 1 is a longitudinal cross section of a distal section of a simplified form of the integrated catheter system.

FIGS. 1 illustrates a simplified integrated catheter system 10 consisting of a balloon angioplasty catheter 12, a stent catheter 30, a guide wire 50 and a stent 15 mounted within stent containment cavity 39. The "over-the wire" balloon angioplasty catheter 12 consists of an inner shaft 21, an outer shaft 22, a balloon 23 radiopaque markers 19A and 19B and an annular passageway 28 that lies between the inner shaft 21 and the outer shaft 22. The markers 19A and 19B are situated to be at the proximal and distal extremities of the stent 15 after it has been placed over the balloon 23. A guide wire 50 is adapted to move slideably through the central lumen 26 of the balloon angioplasty catheter 12. The stent catheter 30 has a pusher tube 32 and an outer tube 31 fixedly attached to the distal end of the pusher tube 32. The outer tube 31 encloses a self-expanding or balloon expandable stent 15. An annular passageway 38 is situated between the outer shaft 22 of the balloon angioplasty catheter 12 and the pusher tube 32 of the stent catheter 30.

FIGS. 2A and 2B are longitudinal cross sections of the distal sections of an integrated catheter system 60 having a balloon angioplasty catheter 20 and a stent catheter 65. The balloon angioplasty catheter 20 has a first radiopaque marker 19 centrally located inside the balloon 23 and a second radiopaque marker 18 mounted just proximal to the balloon 23. The stent catheter 65 has a pusher tube 32 that is attached at its distal end to an outer tube 62 that encloses the stent 15, a spacer tube 68, a radiopaque stop marker 66 and has a nose cone 64 at its distal end. A stent containment cavity 69 is formed within the spacer tube 68, outer tube 62 and the nose cone 64. The central lumen 26 and annular passageways 28 and 38 are identical to those same passageways shown in FIG. 1.

FIG. 2B shows the stent catheter 65 advanced in a distal direction until the first positioning mechanism or stop marker 66 engages the second positioning mechanism or marker 18. As can be seen in FIG. 2B, the engagement of the marker 18 with the marker 66: (1) prevents the stent from being inadvertently released beyond the distal end of the balloon angioplasty catheter 20, (2) accurately centers the stent 15 over the balloon 23, and (3) allows the operator to use the radiopacity of the markers 18 and 66 to indicate that items (1) and (2) above have been accomplished. The length of the spacer tube 68 can be adjusted to assure that items (1) and (2) above can be accomplished.

FIG. 3 is an alternative embodiment of a stent catheter 70 showing a one-piece catheter 71 having a short, thin-walled distal section 72 and a thicker walled tube 73 for most of its length having a stop marker 76 mounted as shown. The distal section 72, the spacer tube 78 and the nose cone 74 form a stent containment cavity 79 that encloses the stent 15.

FIG. 4 is another alternative embodiment of a stent catheter 80 formed from an outer tube 81 fixedly attached to the tube 85 which is fixedly attached to a thin-walled metal tube 83 with a stop marker 86 mounted therebetween. The outer tube 81, spacer tube 88 and the nose cone 84 form a stent containment cavity 89 that contains the stent 15. The embodiments of FIGS. 3 and 4 would function in a manner identical to FIGS. 2A and 2B. One advantage of the embodiment of FIG. 4 is that most of the length of the integrated catheter 80 would be of a smaller diameter.

Figure 5:
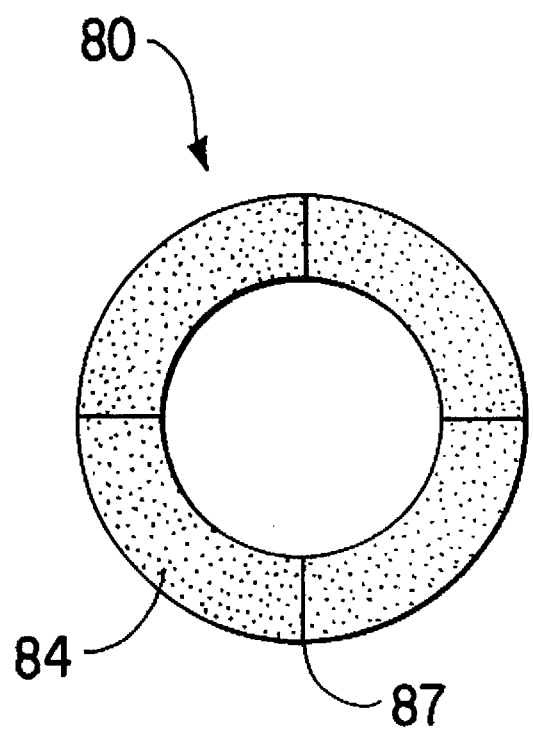
FIG. 5 is a front view showing the nose cone of the integrated catheter system.

FIG. 5 is a front view of the nose cone 84 of the stent catheter 80, the nose cone having four slits 87. The nose cone 84 functions FIGS. 2A, 2B al manner to the nose cones 64 and 74 of FIGS. 2A, 2B and 3. Although FIG. 5 shows four slits in the nose cone 84, as few as 2 or as many as 24 slits could be used. The object of the nose cones 64, 74 or 84 is to retain the stent 15 within the catheters 65, 70 or 80 and to form a tapered front surface which can slide forward with a tight sliding fit over the balloon 23. The purpose of the slits 87 is to allow the stent catheter 80 to be pulled back over the stent without exerting a large proximally directed force onto stent 15.

Figure 6:
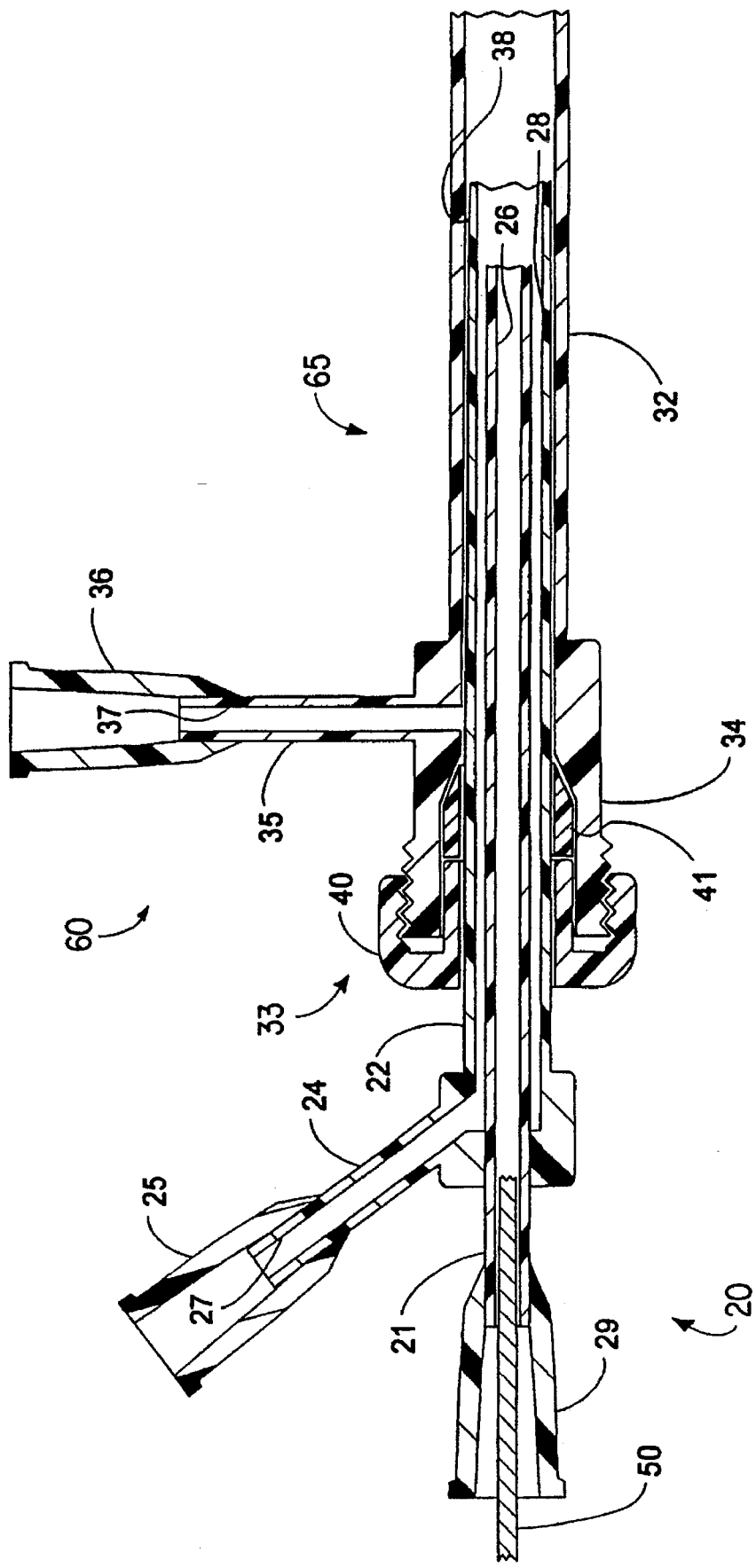
FIG. 6 is longitudinal cross section of a proximal section of the integrated catheter system.

FIG. 6 is a longitudinal cross section of a proximal section of the system 60. The proximal section of the balloon angioplasty catheter 20 shows an outer shaft 22 and an inner shaft 21 having a lumen 26 through which the guide wire 50 can be slideably moved. The inner shaft 21 has a female Luer fitting 29 at its proximal end. The side arm 24 has female Luer fitting 25 and a lumen 27 which is in fluid communication with the annular passageway 28 that lies between the outer surface of the inner shaft 21 and the inner surface of the outer shaft 22. The Luer fitting 29 is used to flush the lumen 26 prior to placement of the guide wire 50. The Luer fitting 25 is attached to a source of pressurized fluid for inflating and deflating the balloon 23.

Also shown in FIG. 6 is the proximal section of the pusher tube 32 that is fixedly attached at its proximal end to a Tuohy-Borst fitting 33. The Tuohy-Borst fitting 33 has a main body 34 and a side arm 35 having a female Luer fitting 35. The side arm 35 has a lumen 37 that is in fluid communication with the annular passageway 38 that lies between the inner surface of the pusher tube 32 and the outer surface of the outer shaft 22 of the balloon angioplasty catheter 20. The Luer fitting 36 makes it possible to flush out the passageway 38 with (typically) a normal saline solution prior to placing the system 10 into an artery of a human body. The nut 40 is screwed onto a threaded section of the main body 34. Tightening down on the nut 40 causes the deformable elastomer gland 41 to be frictionally joined to the outer shaft 22. In this state, the pusher tube 32 will remain in a fixed position relative to the outer shaft 22. When the nut 40 is loosened, the pusher tube 32 can be pushed in a forward direction which, as described below, allows the balloon 23 to deploy the stent 15.

The means for and method of using the integrated catheter system 60 of FIGS. 2A, 2B and 6 is best explained with the aid of FIGS. 7A to 7G inclusive.

Figure 7A:
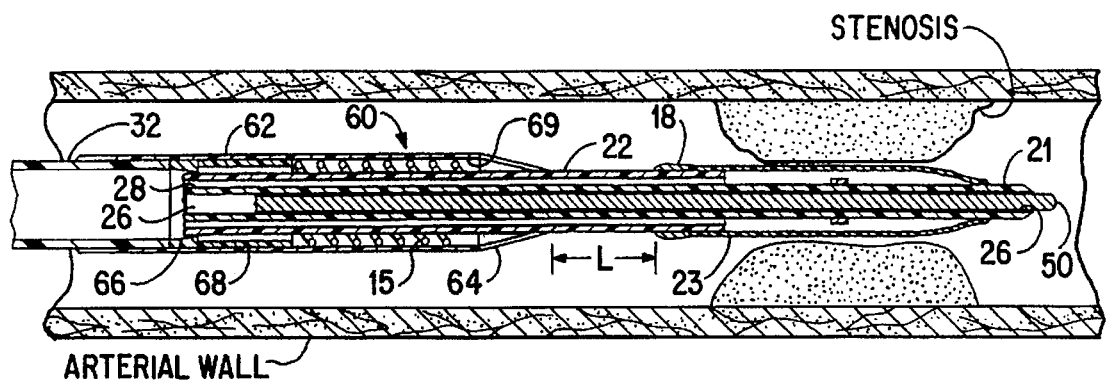
FIG. 7A is a longitudinal cross section of a distal section of the integrated catheter system showing various sections of the balloon angioplasty catheter and the stent catheter and showing an unexpanded balloon placed within an arterial stenosis.

(1) The integrated catheter 60 is advanced in a conventional manner until the balloon 23 lies within an arterial stenosis as shown FIG. 7A. The distance "L" would typically be set between 0.1 and 30 cm with optimum values being between 5 and 10 cm.

Figure 7B:
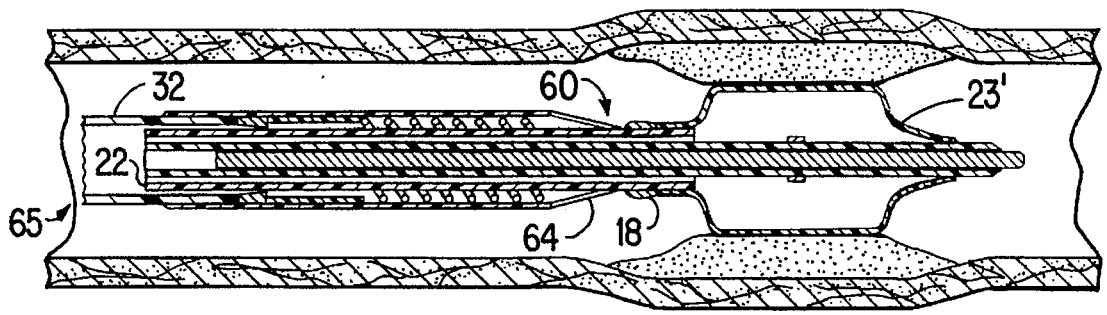
FIG. 7B shows the balloon in its inflated state with the stent catheter advanced in a distal direction until its distal end is adjacent to the proximal end of the balloon.

(2) As shown in FIG. 7B, the balloon is inflated to a low pressure which is just sufficient to allow dilatation of the stenosis to a large enough diameter to allow the stent catheter 65 to pass through the pre-dilated stenosis.

(3) While the balloon is inflated, the stent catheter 65 is advanced over the outer shaft 22 of the balloon angioplasty catheter 20 until the distal end of the nose cone 64 contacts the marker band 18 as shown in FIG. 7B. Advancing the stent catheter 65 is easiest to accomplish when the balloon 23 is inflated.

Figure 7C:
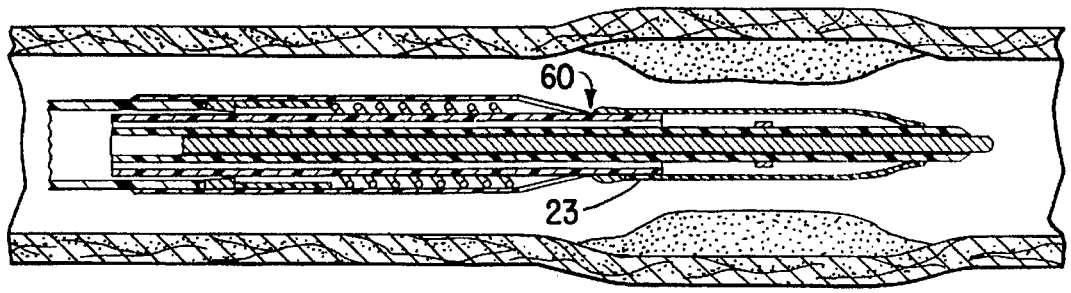
FIG. 7C shows the balloon deflated.

(4) The balloon 23 is deflated as shown in FIG. 7C.

(5) The stent catheter is advanced over the balloon angioplasty catheter 20 until the stop marker 66 cannot be moved more distally because of engagement with the balloon marker 18. In this position the stent 15 is centered over balloon 23. It can be clearly seen from FIGS. 2A and 7D that the stent cannot be advanced beyond the balloon 23. Therefore, it is not possible to inadvertently release the stent beyond the distal end of the balloon angioplasty catheter 20. Thus distal embolization of the stent is precluded.

Figure 7D:
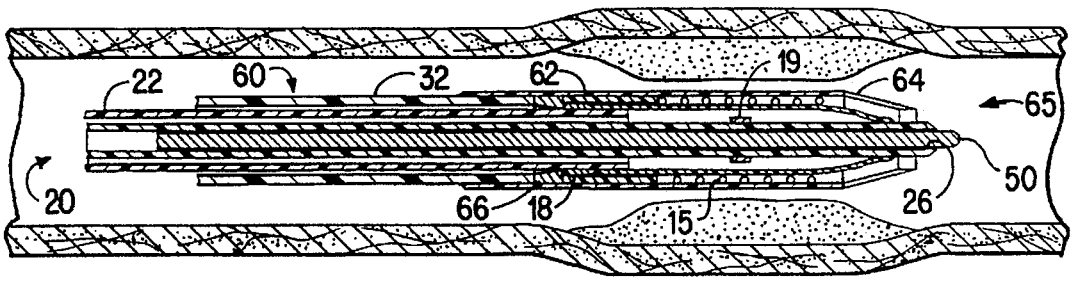
FIG. 7D shows the stent catheter in its most forward position with the stent accurately positioned over the balloon.
Figure 7E:
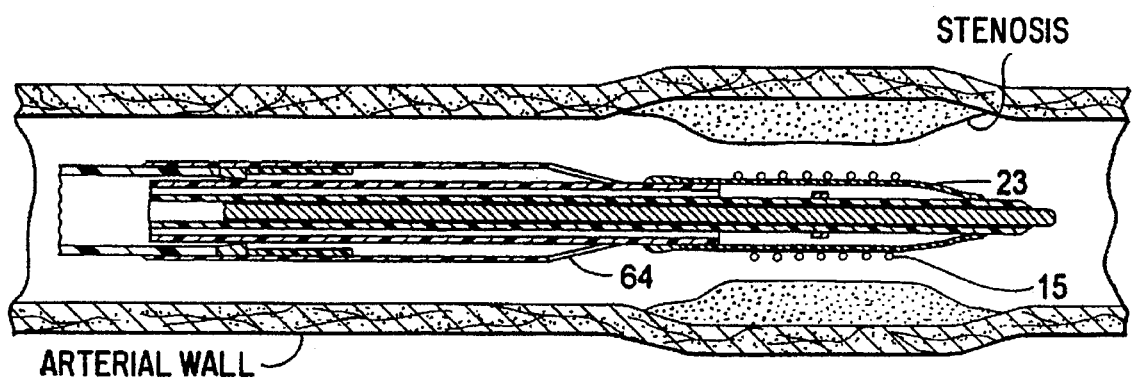
FIG. 7E' shows a balloon expandable stent as it is placed onto the deflated balloon with the stent catheter pulled back.
Figure 7E:
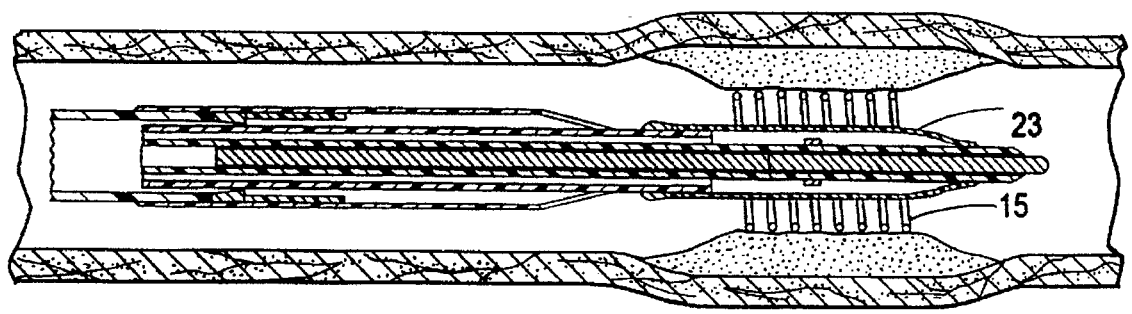

(6) The balloon 23 is then inflated to a very low pressure (typically less than 1 atmosphere) which causes the stent 15 to be retained onto the balloon 23 when the stent catheter is pulled back as shown in FIG. 7E.

(7) If step 6 is accomplished with a self-erecting stent (such as those fabricated from a shape memory alloy such as Nitinol), the stent 15 will deploy radially outward against the inner surface of the dilated stenosis as shown in FIG. 7E'.

Figure 7F:
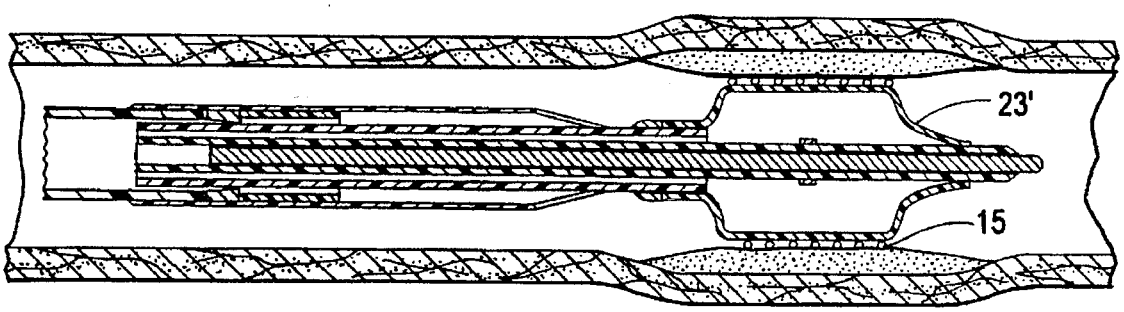
FIG. 7F shows the balloon inflated to high pressure to imbed a balloon expandable stent or a self-expanding stent into the arterial wall.

(8) Irrespective of whether a balloon expandable or self-expanding stent 23 is used, FIG. 7F shows that the balloon 23' is inflated to a high pressure to imbed either type of stent into the stenotic plaque.

Figure 7G:
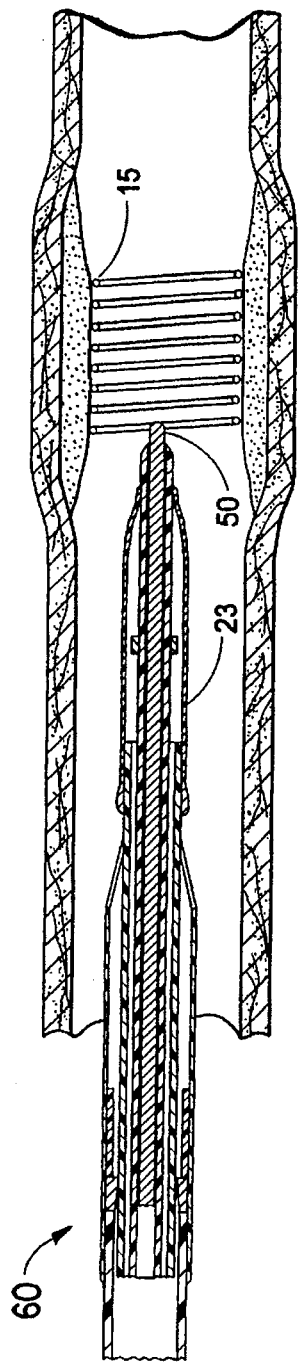
FIG. 7G shows the stent in place with the catheter system being removed from the artery.

(9) FIG. 7G shows the balloon 23 retracted and the integrated catheter system 60 being removed from the artery.

The material(s) selected for the tubes 21, 22, 32 and 62 can be Teflon or an elastomer such as polyurethane or polyethylene. The Tuohy-Borst fittings are typically fabricated from a harder plastic such as PVC or Nylon or a higher durometer of the same elastomer used for the pusher tube 32. The stent 15 should be coated with a covalently bonded heparin coating, as is well known in the art of biomedical surfaces, to reduce thrombotic complications after stent placement. The stent 15 could also have a hydrophilic lubricious coating on at least its exterior surface to reduce frictional forces when the outer sheath 62 is pulled back to release the stent. That is, the stent would optimally have a heparin coating that was also hydrophilic and lubricious.

The length of the integrated catheter 60 is typically 20 to 150 cm depending on the vessel into which it is to be placed. The stent catheter 65 is typically considerably shorter than the length of the balloon catheter 20. When the stent catheter 65 is pulled back to its most proximal position relative to the balloon catheter 20, the distal end of the nose cone 64 should be situated at least 3 cm proximal to the proximal end of the balloon 23 and typically 10 cm back. When the distal end of the nose cone 64 is approximately 10 cm back from the proximal end of the balloon 23, the distal section of the balloon angioplasty catheter 20 can be advanced through an extended length of narrow stenosis and through tortuously curved arteries without the encumbrance and added stiffness of the stent catheter 65 and the stent 15 which otherwise could limit the catheter system's trackability over a guide wire. Once the balloon 23 is placed within a stenosis, and preferably when the balloon is inflated, the stent catheter 65 can be advanced until the distal end of the nose cone is located at the proximal end of the balloon 23.

The diameter of the catheter will typically vary from 1.0 to 10.0 mm depending on its use. The radiopaque marker bands 18, 19, 19A, 19B and 66 are typically made from a dense metal such as an alloy of tantalum, platinum or gold.

A method for using the "over-the-wire" design, integrated catheter 60 for the treatment of an obstructed coronary artery would be as follows:

1. By conventional means, an introducer sheath and a coronary guiding catheter are inserted at the groin and the guiding catheter's distal end is advanced until it is situated within the ostium of a coronary artery.

2. Saline solution is flushed through each of the two annular passageways 28 and 38 and the central lumen 26 of the catheter 20 by means of the three female Luer fittings 25, 29 and 36.

3. A guide wire 50 that has been pre-loaded into the integrated catheter 60 is advanced with the catheter 65 through the guiding catheter, and the guide wire 50 is then advanced through a coronary artery blockage.

4. The catheter 20 is further advanced over the guide wire 50 until the balloon 23 lies within a stenosis as shown in FIG. 7A. This is accomplished with the stent catheter 65 in its most proximal position relative to the balloon 20. The nut 40 of the Tuohy-Borst fitting 33 is initially screwed down tightly to frictionally join the stent catheter 65 to the balloon catheter 20.

5. A fluid pressurization means is then joined to the Luer fitting 25 and the balloon 23 is initially inflated (as shown in FIG. 7B ) to an outside diameter between 2.0 and 3.0 mm depending on the nominal size of the coronary artery in which the blockage occurred. This inflation is to be done at a comparatively low pressure so that the balloon 23 is not inflated to its largest possible diameter.

6. While the balloon 23' is inflated, the nut 40 of the Tuohy-Borst fitting 33 is loosened and the stent catheter 65 is advanced forward in a distal direction thus decreasing the length L until the distal end of nose cone 64 is in contact with the proximal end of the radiopaque marker 18 that is situated just proximal to balloon 23; i.e., L=0. This configuration is shown in FIG. 7B.

7. The balloon 23 is then deflated as shown in FIG. 7C.

Figure 8:
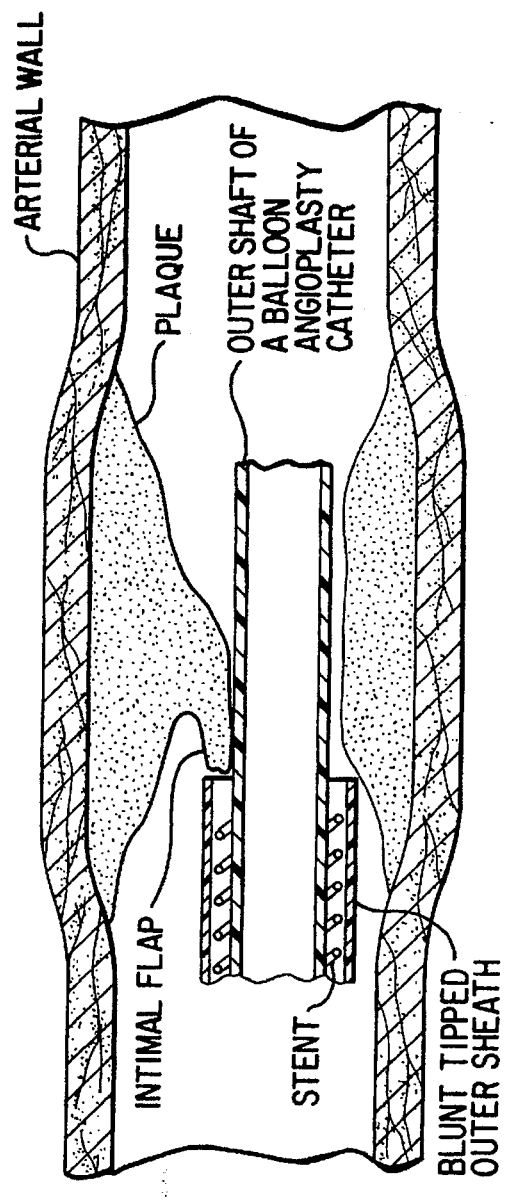
FIG. 8 illustrates how a prior art blunt tipped stent catheter of an integrated stent and balloon angioplasty catheter system can be made dysfunctional because of an intimal flap formed in the plaque after balloon dilatation.

8. The stent catheter 65 is then advanced over the deflated balloon as shown in FIG. 7D. It is important to note that any intimal dissection resulting in an intimal flap will be lifted away from, the surface of the deflated balloon 23 by the pointed distal end of the nose cone 64. This is in contradistinction to all prior art integrated catheter devices which have outer sheaths whose ends are blunt and therefore could have their forward motion stopped by an intimal flap that was in contact with the outer surface of either the balloon or the outer shaft of a balloon angioplasty catheter. This disadvantage of the prior art that can prevent proper functioning of an integrated catheter is shown in FIG. 8.

It should be noted that the balloon angioplasty catheter 20 could be pulled back from the pre-dilated stenosis and angioplasty could be performed once more at that point to provide assurance of an adequate stenotic dilatation. The catheter system 65 could then be advanced to the position shown in FIG. 7D. However, at no time is it required to advance the balloon 23 beyond the dilated stenosis.

It should be noted in FIGS. 2B and 7D that the stop marker 66 has a smaller inside diameter as compared to the outside diameter of the radiopaque marker 18 that is situated just proximal to the balloon 23. Thus stent 15 cannot be advanced beyond the point where it is longitudinally centered over the balloon 23 as shown in FIGS. 2B and 7D. Because the operator cannot advance the stent catheter 65 distally relative to the balloon angioplasty catheter 20 beyond the point where the radiopaque markers 18 and 66 touch, at that point the stent will be automatically positioned at its precisely correct location over the balloon 23. Furthermore, the operator can confirm by fluoroscopy as well as by feel when the radiopaque markers 18 and 66 are in contact with each other. Still further, this simple distally located means prevents the stent from being advanced beyond the distal end of the balloon angioplasty catheter which would be extremely disadvantageous.

9. The stent catheter 65 is then pulled back until the nose cone 64 lies proximal to the proximal end of the balloon 23 as shown in FIG. 7E. The stent 15 will normally stick onto the deflated balloon 23 when the stent catheter 65 is pulled back because the deflated balloon 23 forms "wings" that protrude radially outward even when the balloon 23 is fully deflated. That is, the deflated balloon 23 does not form itself into a tight cylinder around the inner shaft 21, but rather forms a flat shape wherein the "wings" of the deflated balloon are those parts that extend radially outward from the inner shaft 21.

10. To enhance the ability of the balloon 23 to hold onto the stent 15 as the stent catheter 65 is pulled back, the balloon 23 can be slightly inflated to a low pressure between 0.1 and 2 atmospheres prior to pulling back of the stent catheter 65.

11. In the case of the self-expanding stent, (as shown partially expanded in FIG. 7E') the purpose of the balloon expansion is to push back the plaque to allow a comparatively fragile, shape memory metal stent to reach its final fully expanded shape. Until that final shape is achieved, shape memory stents do not exert a sufficiently strong outward radial force to outwardly deform hard plaque. However, once the fully expanded shape of the stent is achieved with the assistance of the balloon 23', shape memory metal stents are sufficiently strong to maintain considerable outward force on the dilated stenosis. At no time does the expanded balloon deform a shape memory metal by exceeding the elastic limit of the metal of the stent. On the other hand, the balloon expandable stent shown in FIGS. 7E and 7F is severely deformed by the expanded balloon 23', thus exceeding the elastic limit of the metal of the stent. This creates a plastic deformation of the stent so that it will retain its expanded shape as shown in FIG. 7G.

12. The balloon 23 is then deflated (as shown in FIG. 7G) and the catheter 60 and the guide wire 50 are removed from the artery and the guiding catheter and introducer sheath are removed from the human body using appropriate methods that are well known in interventional cardiology.

Figure 9:
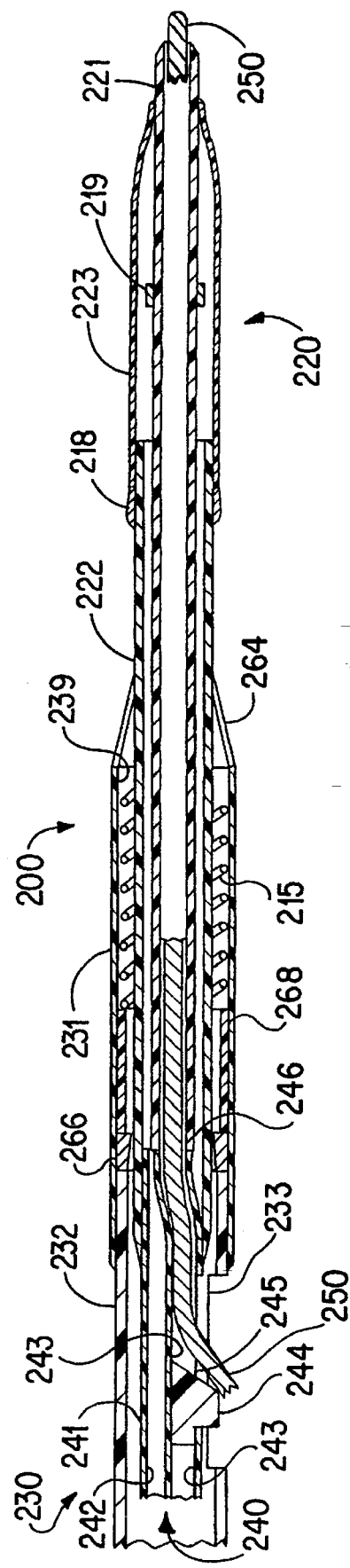
FIG. 9 is a longitudinal cross section of a distal section of a "rapid exchange" embodiment of the integrated catheter system.

As described in steps 1 through 12 above, a single integrated catheter 60 can be used for initial dilatation of a blockage in a vessel at a first and (typically) lower pressure (viz., 6 to 12 atmospheres), for release of a stent within that vessel at the site where the dilatation occurred, and the balloon can be then reinflated to a second and (typically) higher pressure (viz., 10 to 18 atmospheres) to allow a shape memory metal stent or balloon expandable stent to expand to a final, fully expanded state. Thus, the requirement for one or more separate balloon dilatation catheters and a separate stent delivery catheter has been eliminated. FIG. 9 is longitudinal cross section of a "rapid exchange" type of integrated balloon angioplasty catheter and stent system 200. The system 200 uses a conventional rapid exchange balloon angioplasty catheter 220 with the type of stent catheter that has previously been described herein. Specifically, the rapid exchange balloon angioplasty catheter 220 has a distal section which includes a proximal radiopaque marker 218, a balloon centered radiopaque marker 219, an inner shaft 221, an outer shaft 222 and an expandable balloon 223. This distal section is joined to a dual lumen main body 240, having an outer cylinder 241, a balloon inflation lumen 242 and a guide wire lumen 243 that is obstructed near its distal end by a guide wire deflector 244. The guide wire deflector 244 acts as a key in the slot 233 of the stent catheter 230 to prevent axial rotation of the catheter 230 relative to the outer cylinder 241. A thin-walled steel tube 246 joins the inner shaft 221 to the guide wire lumen 243 of the main body 240.

The stent catheter 230 includes a stent 215, a radiopaque stop marker 266, a spacer tube 268, a nose cone 264, an outer tube 231 and a pusher tube 232 into which the guide wire slot 233 is cut. The outer tube 231, spacer tube 268 and nose cone 264 form a stent containment cavity 239 that encloses the stent 215. The guide wire 250 enters through the slot 233 in the pusher tube 232, and then passes through the slot 245 into the distal continuation of the lumen 243, finally emerging from the distal end of the inner shaft 221.

The system 200 operates in exactly the same manner as the previously described system 60, except that the guide wire 250 passes out of the system 200 close to its distal end rather than out its proximal end as shown in FIG. 6 for the conventional over-the-wire balloon angioplasty catheter. The advantage of the system 200 is that it can be used most conveniently after using a rapid exchange balloon angioplasty catheter to perform stenotic dilatation followed by the use of the system 200 in a manner described herein.

It should also be understood that the invention described herein can be used with a variety of angioplasty balloon catheters including those with fixed guide wires at their distal end; i.e., "fixed wire" catheters. The integrated catheter systems described herein could also be used after an initial dilatation of the stenosis using a separate balloon angioplasty catheter as selected by the physician at the time of the vessel opening procedure. Furthermore, the integrated catheter system described herein could be used without pre-dilatation of the stenosis. That is, the stent could be initially centered on the balloon and delivered to the stenosis in that configuration. Then after the stent catheter was pulled back, balloon inflation would dilate the stenosis and deliver the stent into the arterial wall at that location.

It should be further understood that one, two, three or more radiopaque markers could be used with any integrated system design. Furthermore, if a thin-walled metal tube is used for the pusher tube 83 as shown in FIG. 4, either laser or electric discharge machinery could be used to cut through the thin wall of the tube 83 at one or more places along its length to make the tube 83 more flexible. For example, laser machining could be used to make a helical cut through the wall of the tube 83 at the tube's distal section. This would form a flat ribbon helix with greatly increased flexibility. A plastic tube could also be shrunk onto the flat ribbon helix for increased axial rigidity; i.e., so that the laser machined tube 83 would not readily be axially extendible. It is also envisioned that other patterns can be machined into the tube 83 to increase its flexibility such as 330 degree ring cuts with the rings spaced apart by 1 to 50 ram, and the 30 degree (360° minus 330°) section of uncut metal being staggered in position from one ring cut to the next ring cut.

Although the integrated catheter system described herein would perform without applying a slippery coating to any of its parts, applying a slippery coating to the interior surface of the stent containment cavity and/or to the exterior surface of the stent could be used to improve system performance.

Various other modifications, adaptations, and alternative designs are of course possible in light of the above teachings. Therefore, it should be understood at this time that within the scope of the appended claims, the invention may be practiced otherwise than as specifically described herein.

What is claimed is:

1. An integrated catheter system for balloon angioplasty and stent delivery comprising:

a flexible guide wire;

a balloon angioplasty catheter having a distal section including an inflatable balloon having a proximal end and distal end, the distal section also having a passageway through which the guide wire can be slideably moved;

a radially expandable stent;

a stent catheter having a proximal section and a distal section and being generally in the form of an elongated cylinder having a passageway through which the balloon angioplasty catheter can be slideably moved, the stent catheter's distal section including a stent containment cavity into which the stent is placed;

first positioning means secured to said distal section of said stent catheter; and, second positioning means mounted to said distal section of said balloon angioplasty catheter, said first positioning means being displaced responsive to a displacement of said stent catheter to a position adjacent said second positioning means while said second positioning means is maintained in a fixed location, for longitudinally centering the stent over the inflatable balloon.

2. The system of claim 1 wherein the balloon angioplasty catheter is an "over-the-wire" balloon angioplasty catheter.

3. The system of claim 1 wherein the balloon angioplasty catheter includes at least one radiopaque marker.

4. The system of claim 1 wherein the balloon angioplasty catheter includes two radiopaque markers located inside the inflatable balloon that are positioned apart by a distance which is approximately equal to the length of the stent.

5. The system of claim 1 wherein the stent catheter is formed from an elastomer tube throughout a predetermined dimension of the length of the stent catheter.

6. The system of claim 1 wherein the balloon angioplasty catheter includes a radiopaque marker positioned just proximal to the proximal end of the inflatable balloon.

7. The system of claim 6 wherein the distal section of the stent catheter includes at least one radiopaque marker.

8. The system of claim 7 wherein the inside diameter of the stent catheter's radiopaque marker is slightly smaller than the outside diameter of the radiopaque marker located just proximal to the proximal end of the inflatable balloon.

9. The system of claim 8 wherein the stent catheter's radiopaque marker and the radiopaque marker located just proximal to the proximal end of the inflatable balloon cooperate with each other so that when the stent catheter is advanced to its most distal position relative to the balloon angioplasty catheter, the two radiopaque markers touch and the stent is longitudinally centered over the inflatable balloon.

10. The system of claim 8 wherein the two radiopaque markers cooperate to disallow the stent from being advanced beyond the distal end of the balloon angioplasty catheter.

11. An integrated catheter system for balloon angioplasty and stent delivery comprising:

a flexible guide wire;

a balloon angioplasty catheter having a distal section which has an inflatable balloon that has a proximal end and distal end, the distal section also having a passageway through which the guide wire can be slideably moved;

a radially expandable stent;

a stent catheter having a proximal section and a distal section and being generally in the form of an elongated cylinder having a passageway through which the balloon angioplasty catheter can be slideably moved, the stent catheter's distal section including a stent containment cavity into which the stent is placed; and first and second positioning means secured respectively to said stent catheter and said balloon angioplasty catheter for terminating displacement of said stent catheter when said first and second positioning means are brought into abutting relation for longitudinally centering said stent over said inflatable balloon.

12. A method for performing balloon angioplasty and placing a stent within a stenosis in an artery of a human being, the method comprising the following steps:

a) placing a guide wire through a passageway in a balloon angioplasty catheter which balloon angioplasty catheter is placed coaxially through a central passageway of a stent catheter, the balloon angioplasty catheter having a distal section that includes an inflatable balloon and a radiopaque marker located just proximal to the proximal end of the balloon angioplasty catheter, the stent catheter having a distal section wherein is located a radially expandable stent and a radiopaque marker;

b) advancing the guide wire, balloon angioplasty catheter and stent catheter through a vessel of the human body until the distal end of the balloon angioplasty catheter and stent catheter lies proximal to the stenosis;

c) advancing the guide wire through the stenosis;

d) advancing the balloon angioplasty catheter over the guide wire until an inflatable balloon is placed within the stenosis;

e) inflating the inflatable balloon to a first pressure to perform pre-dilatation of the stenosis;

f) deflating the inflatable balloon;

g) advancing the stent catheter over the balloon angioplasty catheter until the stent is properly positioned over the inflatable balloon of the balloon angioplasty catheter;

h) moving the stent catheter back in a proximal direction until the stent is completely uncovered;

i) expanding the inflatable balloon to a second pressure thereby imbedding the stent into the wall of the dilated stenosis;

j) deflating the inflatable balloon; and k) removing the inflatable balloon angioplasty catheter, stent catheter and guide wire from the vessel of the human body.

13. The system of claim 2 further comprising the step of inflating the inflatable balloon to a third and lowest pressure prior to pulling the stent catheter backward in a proximal direction.

14. The system of claim 2 further comprising the step of pulling the balloon angioplasty catheter back in a proximal direction after stenotic dilatation and then performing angiography to determine if the stenosis has been adequately dilated.

15. The system of claim 12 further comprising the step of advancing the stent catheter over the balloon angioplasty catheter when the balloon is inflated until the stent catheter is positioned with its distal end adjacent to the radiopaque marker located just proximal to the proximal end of the balloon of the inflatable balloon angioplasty catheter.

* * * * *